US012685838B2

(12) United States Patent
Yang

(10) Patent No.: US 12,685,838 B2
(45) Date of Patent: Jul. 21, 2026

(54) BRAIN WAVE INDUCTION METHOD

(71) Applicant: Bill Yang, Taipei City (TW)

(72) Inventor: Bill Yang, Taipei City (TW)

(73) Assignee: Cotron Corporation, Taipei City (TW)

( * ) Notice: Subject to any disclaimer, the term of this patent is extended or adjusted under 35 U.S.C. 154(b) by 746 days.

(21) Appl. No.: 18/185,406

(22) Filed: Mar. 17, 2023

(65) Prior Publication Data

US 2024/0261531 A1     Aug. 8, 2024

(30) Foreign Application Priority Data

Feb. 6, 2023   (TW) ................................. 112104096

(51) Int. Cl.
| | |
|---|---|
| *A61M 21/00* | (2006.01) |
| *G10K 11/178* | (2006.01) |
| *H04R 1/10* | (2026.01) |
| *H04R 3/04* | (2006.01) |

(52) U.S. Cl.
CPC ........... *A61M 21/00* (2013.01); *G10K 11/178* (2013.01); *H04R 1/1041* (2013.01); *H04R 1/1083* (2013.01); *H04R 3/04* (2013.01); *A61M 2021/0027* (2013.01); *A61M 2205/33* (2013.01); *A61M 2205/42* (2013.01); *G10K 2210/1081* (2013.01); *H04R 2420/07* (2013.01); *H04R 2460/01* (2013.01)

(58) Field of Classification Search
CPC .......... A61M 21/00; A61M 2021/0027; A61M 2205/33; A61M 2205/42; G10K 11/178; G10K 2210/1081; H04R 1/1041; H04R 1/1083; H04R 3/04; H04R 2420/07; H04R 2460/01
See application file for complete search history.

(56) References Cited

U.S. PATENT DOCUMENTS

| | | | |
|---|---|---|---|
| 5,135,468 | A | 8/1992 | Meissner |
| 9,288,588 | B2 | 3/2016 | Mesfin |
| 10,264,357 | B1 | 4/2019 | Su |
| 11,218,789 | B1 * | 1/2022 | Ko ........................ H04R 1/086 |
| 12,363,481 | B2 | 7/2025 | Pan |
| 2006/0116597 | A1 | 6/2006 | Vesely et al. |
| 2006/0252978 | A1 | 11/2006 | Vesely et al. |
| 2007/0282216 | A1 | 12/2007 | Vesely et al. |

(Continued)

FOREIGN PATENT DOCUMENTS

| | | |
|---|---|---|
| CN | 200983674 | 11/2007 |
| CN | 202364375 | 8/2012 |

(Continued)

OTHER PUBLICATIONS

"Office Action of Russia Related Application, Application No. 2024102821", issued on Aug. 28, 2024, p. 1-p. 12.

(Continued)

*Primary Examiner* — Andrew Sniezek
(74) *Attorney, Agent, or Firm* — JCIPRNET

(57) ABSTRACT

A brain wave induction method is provided. In the method, a first sound wave to a left ear of a user and a second sound wave to a right ear of the user are simultaneously provided. There is a frequency difference between a first frequency of the first sound wave and a second frequency of the second sound wave. The frequency difference is automatically changed along with time.

13 Claims, 11 Drawing Sheets

Time (minute)

(56)                    References Cited

U.S. PATENT DOCUMENTS

| | | |
|---|---|---|
| 2008/0304691 A1 | 12/2008 | Lai |
| 2010/0239096 A1 | 9/2010 | Jeon et al. |
| 2013/0010967 A1 | 1/2013 | Atwater et al. |
| 2013/0202119 A1 | 8/2013 | Thiede |
| 2014/0350706 A1 | 11/2014 | Morishima |
| 2015/0071448 A1 | 3/2015 | Mesfin |
| 2016/0030702 A1 | 2/2016 | Yang |
| 2016/0110349 A1 | 4/2016 | Norman-Rosedam |
| 2017/0173296 A1 | 6/2017 | Park et al. |
| 2019/0282779 A1 | 9/2019 | Holloway |
| 2019/0328996 A1 | 10/2019 | Lee et al. |
| 2020/0382884 A1 | 12/2020 | Chang et al. |
| 2021/0021947 A1 | 1/2021 | Kao et al. |
| 2021/0030998 A1 | 2/2021 | Wong |
| 2021/0152920 A1 | 5/2021 | Gong et al. |
| 2021/0218380 A1 | 7/2021 | Chao et al. |
| 2021/0338970 A1 | 11/2021 | Radtke |
| 2021/0377642 A1 | 12/2021 | Luo et al. |
| 2022/0088343 A1 | 3/2022 | Kao et al. |
| 2022/0176151 A1 | 6/2022 | Brown et al. |
| 2023/0001127 A1 | 1/2023 | Khalil |
| 2024/0267670 A1 | 8/2024 | Yang |

FOREIGN PATENT DOCUMENTS

| | | |
|---|---|---|
| CN | 103493512 | 1/2014 |
| CN | 103691044 | 4/2014 |
| CN | 103796702 | 5/2014 |
| CN | 206370925 | 8/2017 |
| CN | 109621153 | 4/2019 |
| CN | 109756880 | 5/2019 |
| CN | 110246508 | 9/2019 |
| CN | 111821556 | 10/2020 |
| CN | 113223541 | 8/2021 |
| CN | 217307842 | 8/2022 |
| DE | 10100663 | 7/2002 |
| DE | 102011052186 | 1/2013 |
| EP | 2362678 | 8/2011 |
| EP | 2777165 | 4/2018 |
| EP | 3248577 | 9/2021 |
| IN | 201641029383 | 3/2018 |
| JP | H0833714 | 2/1996 |
| JP | H08196638 | 8/1996 |
| JP | 2000197171 | 7/2000 |
| JP | 2001014314 | 1/2001 |
| JP | 2005279286 | 10/2005 |
| JP | 2005334163 | 12/2005 |
| JP | 3142675 | 6/2008 |
| JP | 2011259409 | 12/2011 |
| JP | 2014507889 | 3/2014 |
| JP | 2015506142 | 2/2015 |
| JP | 2017111414 | 6/2017 |
| JP | 2017121529 | 7/2017 |
| JP | 2020110582 | 7/2020 |
| JP | 3236581 | 3/2022 |
| JP | 2022529033 | 6/2022 |
| KR | 20070112581 | 11/2007 |
| KR | 20090041667 | 4/2009 |
| KR | 20160117882 | 10/2016 |
| KR | 101828952 | 2/2018 |
| TW | 201640918 | 11/2016 |
| TW | 202127906 | 7/2021 |
| WO | 0237449 | 5/2002 |
| WO | 2014160757 | 10/2014 |
| WO | 2018030404 | 2/2018 |
| WO | 2018159519 | 9/2018 |
| WO | 2019045857 | 3/2019 |
| WO | 2021192072 | 9/2021 |
| WO | 2022141552 | 7/2022 |

OTHER PUBLICATIONS

"Office Action of Russia Related Application, Application No. 2024135054/28(077819)", issued on Apr. 17, 2025, p. 1-p. 9.

F. R. On et al., "Binaural Beat Effect on Brainwaves based on EEG", 2013 IEEE 9th International Colloquium on Signal Processing and its Applications, Mar. 8-10, 2013, pp. 339-343.

"Office Action of Great Britain Related Application, Application No. 2401075.3", issued on Jul. 16, 2024, p. 1-p. 7.

"Notice of allowance of Japan Related Application, Application No. 2024005860", issued on Jun. 25, 2025, p. 1-p. 3.

"Office Action of Russia Related Application, Application No. 2024135046", issued on Jul. 1, 2025, p. 1-p. 12.

"Search Report of Europe Counterpart Application", issued on Sep. 18, 2023, p. 1-p. 8.

"Office Action of Taiwan Counterpart Application", issued on Nov. 9, 2023, p. 1-p. 9.

"Office Action of Germany Counterpart Application", issued on Jan. 2, 2024, p. 1-p. 8.

"Office Action of Japan Counterpart Application", issued on Jan. 11, 2024, p. 1-p. 3.

"Office Action of Japan Related Application, Application No. 2024-005860", issued on Mar. 5, 2025, p. 1-p. 7.

"Office Action of Taiwan Related Application, Application No. 113100246", issued on Mar. 5, 2025, p. 1-p. 10.

"Search Report of Europe Related Application, Application No. 24150314.3", issued on Mar. 1, 2024, p. 1-p. 9.

"Office Action of U.S. related Application, U.S. Appl. No. 18/395,612", issued on Oct. 3, 2025, p. 1-p. 11.

"Office Action of Korea Related Application, Application No. 10-2024-0017210", issued on Aug. 24, 2025, p. 1-p. 8.

* cited by examiner

BRAIN WAVE INDUCTION METHOD

CROSS-REFERENCE TO RELATED APPLICATION

This application claims the priority benefit of Taiwan application no. 112104096, filed on Feb. 6, 2023. The entirety of the above-mentioned patent application is hereby incorporated by reference herein and made a part of this specification.

BACKGROUND

Technical Field

The invention relates to a method, and particularly relates to a brain wave induction method.

Description of Related Art

Along with rapid advancement of science and technology, emotional problems and sleep problems have also become problems that many people must face. At present, medication is mainly used to solve the emotional problems and the sleep problems. However, the medication has limited effectiveness and often comes with side effects.

Studies have found that brain waves emitted by a brain will be different in different emotions and sleep stages. Moreover, if the brain may be induced to produce specific brain waves, it may also affect or even change people's emotions and sleep stages, thereby mitigating the emotional problems and the sleep problems. Therefore, how to effectively induce the brain to produce specific brain waves has become a subject worthy of exploration.

SUMMARY

The invention is directed to a brain wave induction method, which is adapted to mitigate a problem of poor efficiency of brain wave induction.

The invention provides a brain wave induction method. The method includes: simultaneously providing a first sound wave to a left ear of a user and a second sound wave to a right ear of the user. There is a frequency difference between a first frequency of the first sound wave and a second frequency of the second sound wave. The frequency difference is automatically changed along with time.

In an embodiment of the invention, the frequency difference is changed multi-segmentally along with time.

In an embodiment of the invention, the frequency difference is remained unchanged for 5 seconds to 120 seconds after each change.

In an embodiment of the invention, a change amount of each change in the frequency difference is 0.1 Hz, 0.2 Hz, 0.5 Hz, or 1 Hz.

In an embodiment of the invention, a change amount of each change in the frequency difference is between 0.1 Hz and 1 Hz.

In an embodiment of the invention, the frequency difference is changed between 0.5 Hz and 4 Hz, between 4 Hz and 8 Hz, between 8 Hz and 12 Hz, or between 12 Hz and 20 Hz.

In an embodiment of the invention, the frequency difference is gradually reduced from 12 Hz to 0.5 Hz.

In an embodiment of the invention, the frequency difference is reduced by 0.1 Hz each time.

In an embodiment of the invention, the frequency difference remains unchanged for 16 seconds after each change.

In an embodiment of the invention, the brain wave induction method is to respectively provide the first sound wave and the second sound wave to the left ear and the right ear of the user through an earphone.

In an embodiment of the invention, the earphone has an active noise cancellation (ANC) function.

In an embodiment of the invention, the brain wave induction method is to respectively provide the first sound wave and the second sound wave to the left ear and the right ear of the user through a wireless earphone.

In an embodiment of the invention, the brain wave induction method is to respectively provide the first sound wave and the second sound wave to the left ear and the right ear of the user through a Bluetooth earphone.

In an embodiment of the invention, after respectively providing the first sound wave and the second sound wave to the left ear and the right ear of the user for a predetermined time, provision of the first sound wave and the second sound wave is automatically stopped.

In an embodiment of the invention, the first sound wave and the second sound wave are respectively generated after performing a frequency adjustment on a self-selected audio of the user.

In an embodiment of the invention, the brain wave induction method further includes providing a first background sound wave to the left ear of the user and a second background sound wave to the right ear of the user while providing the first sound wave and the second sound wave. The frequency difference is provided between a third frequency of the first background sound wave and a fourth frequency of the second background sound wave.

Based on the above description, in the brain wave induction method of the invention, the frequency difference is changed automatically along with time, and may successfully induce brains of most users to produce specific brain waves.

DESCRIPTION OF THE EMBODIMENTS

An embodiment of the invention provides a brain wave induction method. The method includes: simultaneously providing a first sound wave to a left ear of a user and a second sound wave to a right ear of the user. A frequency of the first sound wave is a first frequency, and a frequency of the second sound wave is a second frequency. There is a frequency difference between the first frequency and the second frequency. The frequency difference is automatically changed along with time. Namely, the frequency difference is not constant. Moreover, without human intervention, the frequency difference is automatically changed according to a preset method.

Brain waves refer to electrical swing generated when nerve cells in a human brain are active, which may also be referred to as a rhythm of brain cell activity. The human brain always produces brain waves. Classified by frequency, brain waves include at least β wave, α wave, θ wave, δ wave, and γ wave. Generally, when a person is in a third stage of a non-rapid eye movement sleep, the brain wave is usually a δ wave (with a frequency between 0.5 Hz and 4 Hz). When a person is in a deep sleep dreaming, deep meditation, a state of intense subjectivity, etc., the brain wave is usually a θ wave (with a frequency between 4 Hz and 8 Hz). When a person is in a state of dazed mind before going to sleep, gradually blurred consciousness, flashes of inspiration, relaxed body and focused mind, etc., the brain wave is usually an α wave. When a person is in a relaxed but focused state, a state of sorting out previously received information, etc., the brain wave is usually a β wave. However, studies have also found that when the human brain is induced to produce different brain waves, it also affects the state of the person in turn. For example, when the human brain is induced to produce the α wave, the person is also brought into a state of flashes of inspiration, relaxed body and focused mind, etc.

Figure 1A:
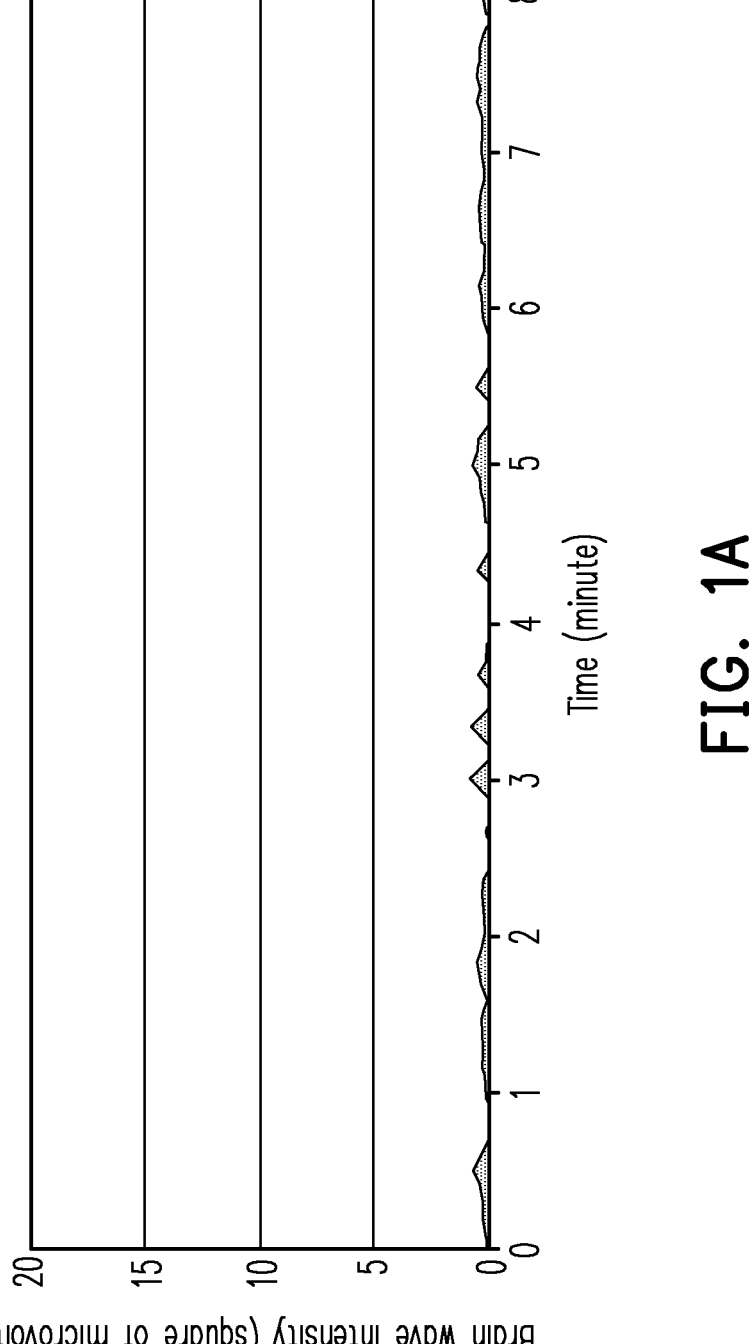
FIG. 1A is an experimental result of a comparative example 1 using a brain wave induction method of the prior art.

Based on the above reasons, the prior art attempts to respectively provide two kinds of sound waves with different frequencies to a left ear and a right ear of the user, and make a frequency difference of the two sound waves to correspond to a frequency of the brain wave desired to be induced. However, the prior art keeps the frequency difference between the two sound waves at a constant value. FIG. 1A is an experimental result of a comparative example 1 using a brain wave induction method of the prior art. In the comparative example 1, the frequency difference is kept constant at 8 Hz. Referring to FIG. 1A, within 8 minutes of continuously inputting such frequency difference, almost no α wave is induced in a brain of a testee.

Figure 1B:
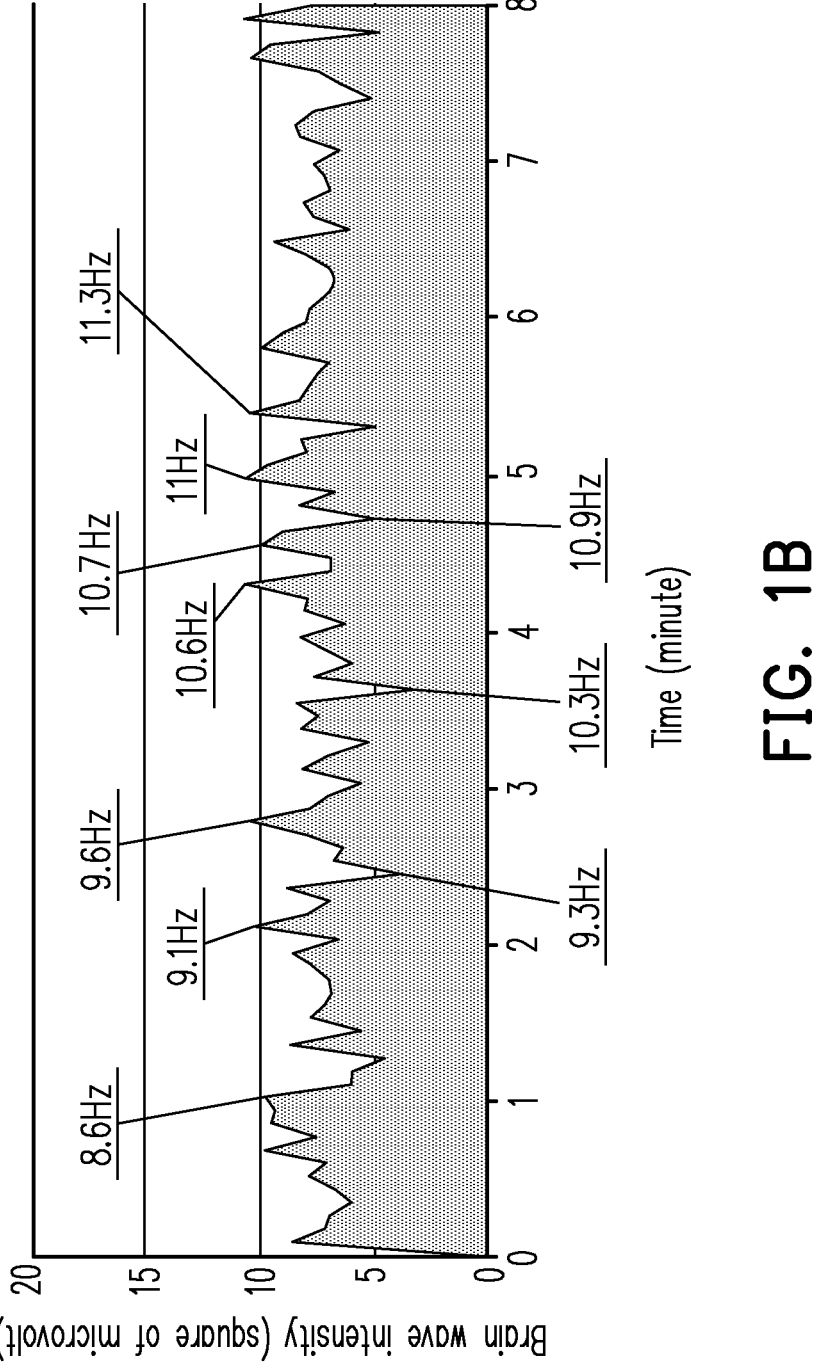
FIG. 1B is an experimental result of an experimental example 1 using a brain wave induction method of the embodiment.

Conversely, in the brain wave induction method of the embodiment, the frequency difference between the first frequency and the second frequency is changed automatically along with time. FIG. 1B is an experimental result of an experimental example 1 using a brain wave induction method of the embodiment. The testees in the comparative example 1 and the experimental example 1 are the same person. In the experimental example 1, the frequency difference is automatically and segmentally changed between 8 Hz and 12 Hz, a change amount of each change in the frequency difference is 0.1 Hz, and the same frequency difference is remained unchanged for 10 seconds after each change. Referring to FIG. 1B, within 8 minutes of continuously inputting the frequency difference in the way of the experimental example 1, it may be detected that the brain of the testee is induced with α waves in almost most of the time periods, especially when the frequency difference is at 8.6 Hz, 9.1 Hz, 9.6 Hz, 10.6 Hz, 10.7 Hz, 11 Hz and 11.3 Hz, the energy of the induced α waves are particularly high.

Comparing the experimental result of the comparative example 1 in FIG. 1A and the experimental result of the experimental example 1 in FIG. 1B, it may be clearly seen that the brain wave induction method of the embodiment is more efficient in inducing brain waves than the prior art. Namely, in the brain wave induction method of the embodiment, the automatic change of the frequency difference along with time may obviously and effectively induce brain waves.

Figure 6:
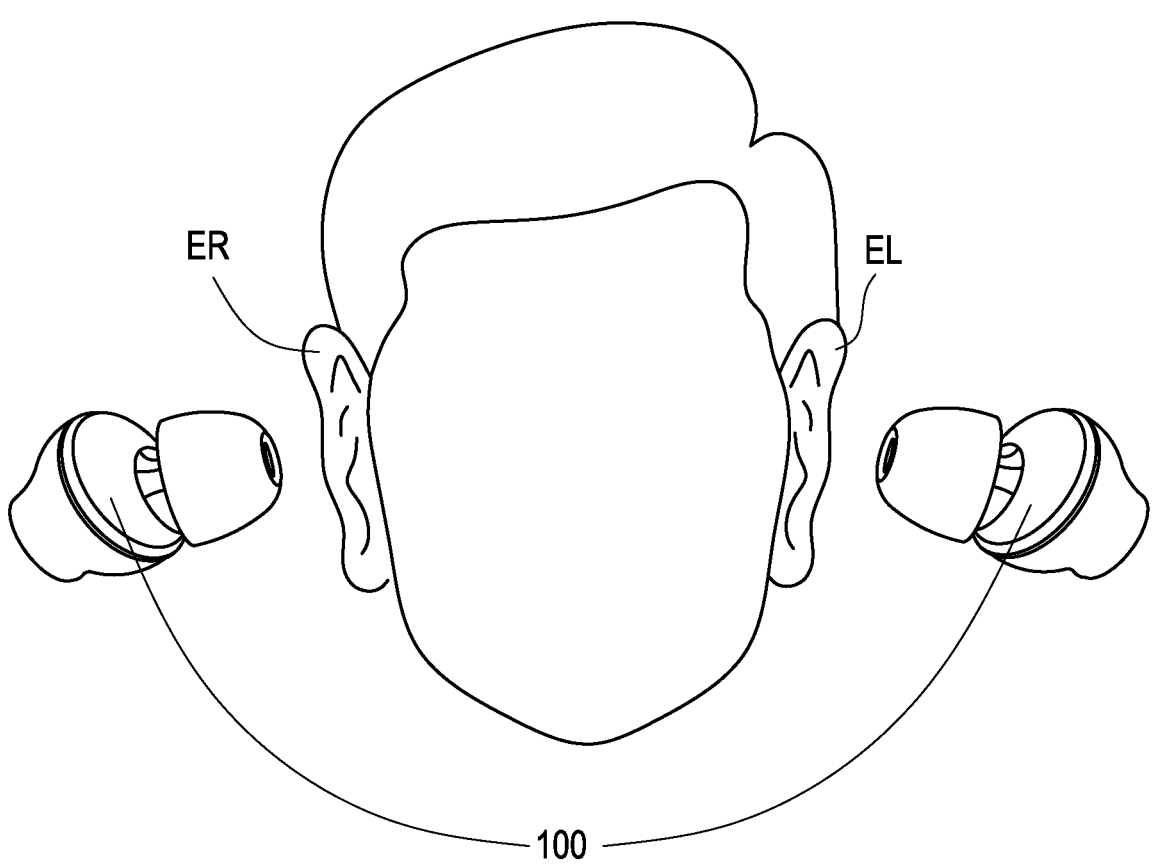
FIG. 6 is a schematic view of an earphone for the brain wave induction method of the embodiment.

FIG. 6 is a schematic view of an earphone for the brain wave induction method of the embodiment. Referring to FIG. 6, in order to provide two kinds of sound waves of different frequencies to the left ear EL and the right ear ER of the user, an earphone 100 may be used, such as an earmuff earphone, an earplug earphone, an in-ear earphone or other different types of earphones, and the earphone may be, for example, a wired earphone, a Bluetooth earphone, or other wireless earphones. The earphone 100 has an active noise cancellation (ANC) function to avoid being affected by ambient noise.

In various embodiments of the invention, the user may select an audio, such as a pop song, a classical music, a radio program or any other type of audio. After receiving the self-selected audio, for example, a sound wave of the self-selected audio to be provided to the left ear is up-converted to generate a first sound wave, and a sound wave of the self-selected audio to be provided to the right ear is down-converted to generate a second sound wave, so that there is a desired frequency difference between a first frequency of the first sound wave and a second frequency of the second sound wave, and the first sound wave and the second sound wave are respectively provided to the left ear and the right ear of the user. Alternatively, the sound wave of the self-selected audio to be provided to the left ear may be down-converted to generate the first sound wave, and the sound wave of the self-selected audio to be provided to the right ear is up-converted to generate the second sound wave, so that there is the desired frequency difference between the first frequency of the first sound wave and the second frequency of the second sound wave. Alternatively, the sound wave of the self-selected audio to be provided to the left ear may be up-converted to generate the first sound wave, and the sound wave of the self-selected audio to be provided to the right ear is directly taken as the second sound wave, so that there is the desired frequency difference between the first frequency of the first sound wave and the second frequency of the second sound wave. Alternatively, the sound wave of the self-selected audio to be provided to the left ear is directly taken as the first sound wave, and the sound wave of the self-selected audio to be provided to the right ear may be down-converted to generate the second sound wave, so that there is the desired frequency difference between the first frequency of the first sound wave and the second frequency of the second sound wave. No matter what method is adopted, the spirit of the invention is met as long as there is the desired frequency difference between the first frequency of the first sound wave and the second frequency of the second sound wave.

In addition, since the user-self-selected audio may have blank parts. In order to continue to induce brain waves in the blank parts, a first background sound wave may be provided to the left ear of the user and a second background sound wave may be provided to the right ear of the user while providing the first sound wave and the second sound wave. A third frequency of the first background sound wave and a fourth frequency of the second background sound wave have a desired frequency difference. Since the background sound wave is continuous and has no blank part, it may continue to induce brain waves in the blank parts of the user's self-selected audio. The background sound waves are, for example, sound waves that are not likely to affect the self-selected audio such as a wind blowing sound, an ocean wave sound, etc.

Figure 2A:
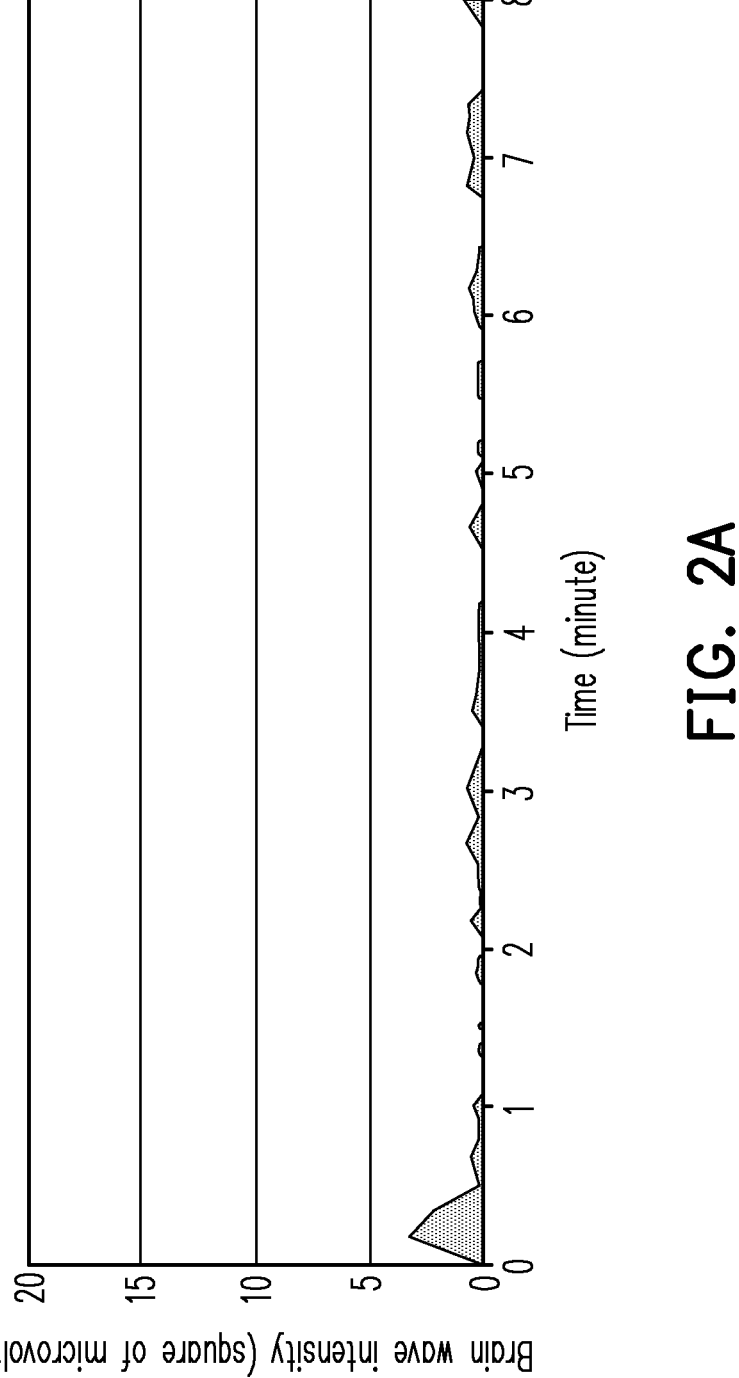
FIG. 2A is an experimental result of a comparative example 2 using the brain wave induction method of the prior art.

FIG. 2A is an experimental result of a comparative example 2 using the brain wave induction method of the prior art. In the comparative example 2, the frequency difference was kept constant at 8 Hz, but the testee is different from that of the comparative example 1. Referring to FIG. 2A, within 8 minutes of continuously inputting the frequency difference, the α wave is only induced in the brain of the testee at the beginning, but a duration thereof is less than 30 seconds.

Figure 2B:
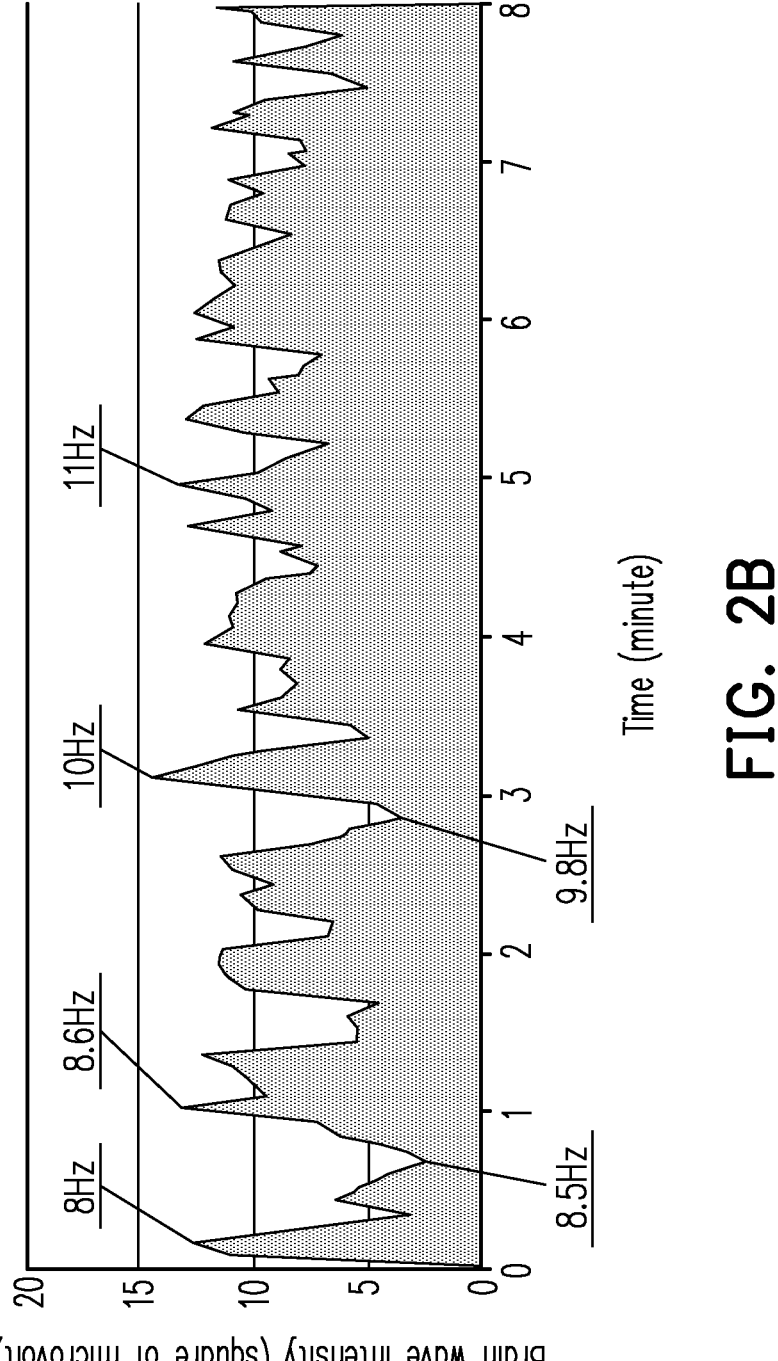
FIG. 2B is an experimental result of an experimental example 2 using the brain wave induction method of the embodiment.

FIG. 2B is an experimental result of an experimental example 2 using the brain wave induction method of the embodiment. The testees in the comparative example 2 and experimental example 2 are the same person. In the experimental example 2, the frequency difference is automatically and segmentally changed between 8 Hz and 12 Hz, a change amount of each change in the frequency difference is 0.1 Hz, and the same frequency difference is remained unchanged for 10 seconds after each change. Referring to FIG. 2B, within 8 minutes of continuously inputting the frequency difference in the manner of the experimental example 2, it may be detected that the brain of the testee is induced with α waves in almost most of the time periods, especially when the frequency difference is at 8 Hz, 8.6 Hz, 10 Hz and 11 Hz, the energy of the induced α waves are particularly high.

Comparing the experimental result of the comparative example 2 in FIG. 2A and the experimental result of the experimental example 2 in FIG. 2B, it may be clearly seen that the brain wave induction method of the embodiment is more efficient in inducing brain waves than the prior art. Namely, in the brain wave induction method of the embodiment, the automatic change of the frequency difference along with time may obviously and effectively induce brain waves.

In addition, with reference to the experimental result of the experimental example 1 of FIG. 1B and the experimental result of the experimental example 2 of FIG. 2B, it may also be found that the first sound wave and the second sound wave of different frequency differences have different effects on brain wave induction of different testees. Therefore, in the prior art, the constant frequency difference is used to induce the brain waves of different users, which may not have a good induction effect. Conversely, the brain wave induction method of the embodiment induces the brain waves of the user with an automatically changing frequency difference, even if the brain wave of a certain user does not have a good induction effect at a specific frequency difference, along with the automatic change of the frequency difference, the method of the invention may basically have a good induction effect on the user's brain during the changing period.

In addition, each user's brain may not only have a good induction effect for a single frequency difference, but usually may have good induction effect for multiple frequency differences. Since the brain wave induction method of the embodiment induces the user's brain waves with automatically changing frequency differences, better induction effects may be produced at multiple frequency differences. Moreover, it may also be seen from the comparative example 2 in FIG. 2A that even if the testee has a good induction effect for the input single frequency difference, the duration thereof may not be long. Since the brain wave induction method of the embodiment induces the brain waves of the user with the automatically changing frequency difference, another frequency difference may be switched to produce the good induction effect again after the user's brain is tired. Finally, the brain wave induction method of the embodiment may produce good brain wave induction effects in a longer period of time.

In the embodiment, the frequency difference is changed multi-segmentally along with time, i.e., there is a relatively obvious difference between the frequency difference at a previous moment and the frequency difference at a next moment. A change amount of each change in the frequency difference may be between 0.1 Hz and 1 Hz., such as 0.1 Hz, 0.2 Hz, 0.5 Hz, or 1 Hz. In other embodiments, the frequency difference may also change non-segmentally along with time.

TABLE ONE

| | | Time of inducing brain wave | | | | No |
| --- | --- | --- | --- | --- | --- | --- |
| | | 5~30 s | 30~60 s | 60~90 s | 90~120 s | induction |
| Frequency | 2 Hz | 12 people | 7 people | 2 people | 2 people | 2 people |
| of | 6 Hz | 10 people | 8 people | 1 people | 3 people | 3 people |
| inducing | 10 Hz | 11 people | 7 people | 3 people | 2 people | 2 people |
| brain | 20 Hz | 9 people | 8 people | 4 people | 1 people | 3 people |
| wave | | | | | | |

Referring to the table 1 above, when 25 testees are tested for brain wave induction with sound waves of a constant frequency difference, 9-12 people are detected to induce brain waves of 2 Hz, 6 Hz, 10 Hz and/or 20 Hz between 5 and 30 seconds, 7-8 people are detected to induce brain waves between 30 and 60 seconds, 1-4 people are detected to induce brain waves between 60 and 90 seconds, and 1-3 people are detected to induce brain waves between 90 and 120 seconds. However, in the first 5 seconds of the test, no one is detected to induce brain waves of 2 Hz, 6 Hz, 10 Hz or 20 Hz, and after testing for more than 120 seconds, there are still 2-3 people who have not been detected to induce brain waves of 2 Hz, 6 Hz, 10 Hz or 20 Hz. Namely, if the test lasts for less than 5 seconds, basically the purpose of inducing brain waves cannot be achieved. On the other hand, if the testee still has no brain waves induced after the test is maintained for 120 seconds, the purpose of inducing brain waves cannot be achieved by continuing the test.

In each embodiment of the invention, after inducing the brain waves of the user with a sound wave of a constant frequency difference for a predetermined time, the provision of the first sound wave and the second sound wave may be automatically stopped, but the invention is not limited thereto.

Figure 3A:
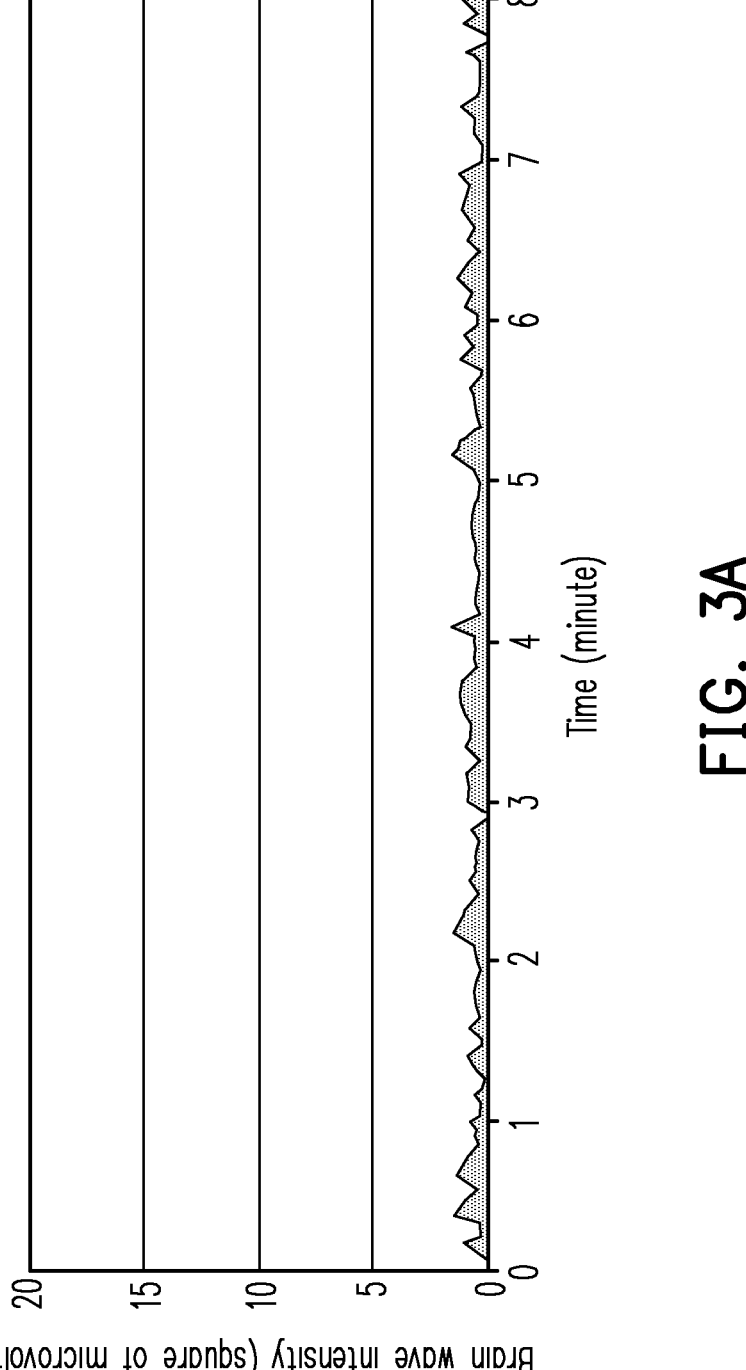
FIG. 3A is an experimental result of an experimental example 3 using the brain wave induction method of the embodiment.

FIG. 3A is an experimental result of an experimental example 3 using the brain wave induction method of the embodiment. In the experimental example 3, the frequency difference is automatically and segmentally changed between 8 Hz and 12 Hz, a change amount of each change in the frequency difference is 0.1 Hz, and the same frequency difference is remained unchanged for 4 seconds after each change. Referring to FIG. 3A, within 8 minutes of continuously inputting the frequency difference in the manner of the experimental example 3, it may be detected that the brain of the testee is induced with α waves in almost most of the time periods, but the energy of the induced α waves is very low.

Figure 3B:
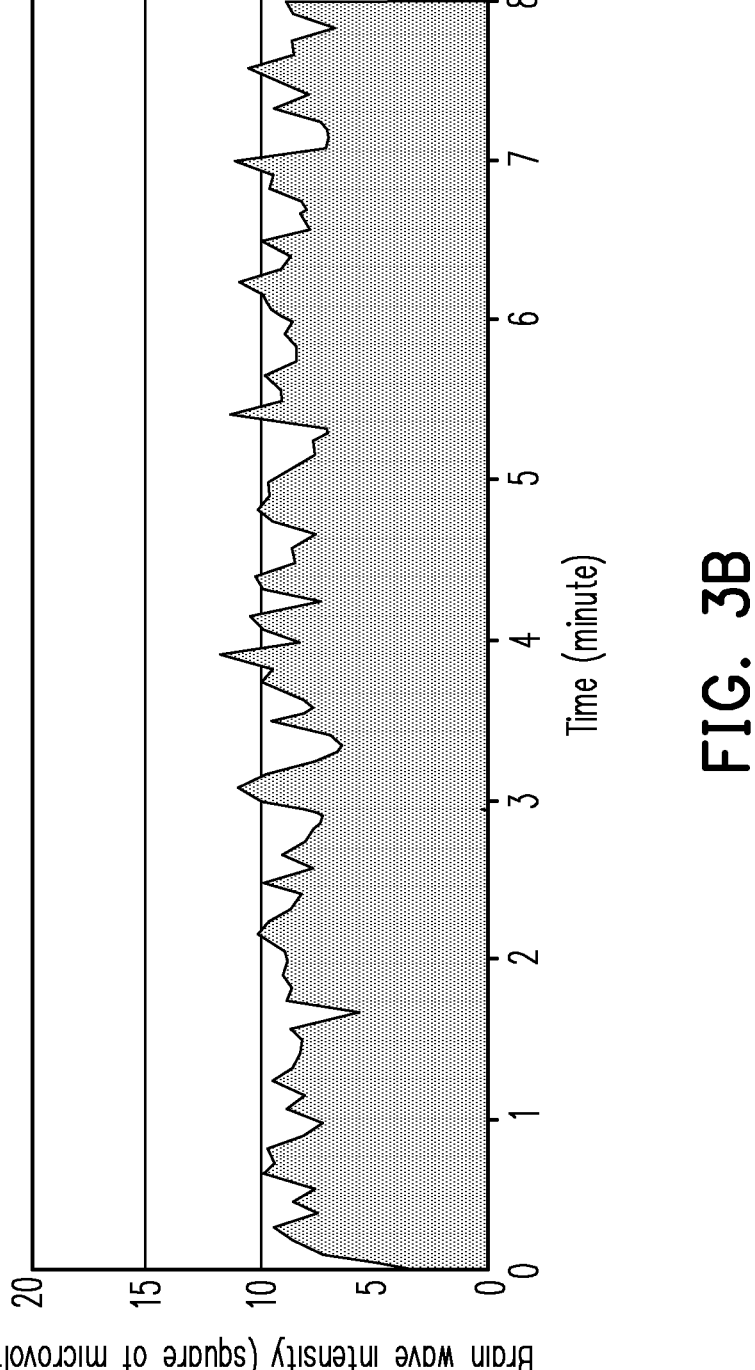
FIG. 3B is an experimental result of an experimental example 4 using the brain wave induction method of the embodiment.

FIG. 3B is an experimental result of an experimental example 4 using the brain wave induction method of the embodiment. The testees in the experimental example 3 and the experimental example 4 are the same person. In the experimental example 4, the frequency difference is automatically and segmentally changed between 8 Hz and 12 Hz, a change amount of each change in the frequency difference is 0.1 Hz, and the same frequency difference is remained unchanged for 5 seconds after each change. Referring to FIG. 3B, within 8 minutes of continuously inputting the frequency difference in the manner of the experimental example 4, it may be detected that the brain of the testee is induced with α waves in almost most of the time periods, and the energy of the induced α waves is continuously maintained at a high level.

Based on the analysis result of table 1 and by comparing the experimental result of the experimental example 3 of FIG. 3A and the experimental result of the experimental example 4 of FIG. 3B, in the brain wave induction method of the embodiment, the same frequency difference is, for example, remained unchanged for 5 seconds to 120 seconds after each change, which may achieve a better brain wave induction efficiency, but the invention is not limited thereto.

In the embodiment, the frequency difference may be changed between 0.5 Hz to 4 Hz to induce δ waves, the frequency difference may be changed between 4 Hz to 8 Hz to induce θ waves, the frequency difference may be changed between 8 Hz and 12 Hz to induce α waves, and the frequency difference may be changed between 12 Hz and 20 Hz to induce β waves. In addition, in the embodiment, the frequency difference may be changed back and forth within a specific interval, and is not limited to be only gradually increased or only gradually decreased.

In a brain wave induction method of another embodiment of the invention, the frequency difference is gradually decreased from a larger value to a target value, for example, gradually decreased from 12 Hz to 0.5 Hz. When the frequency difference becomes smaller than the target value, the brain wave induction procedure may be ended. In the embodiment, the frequency difference may be automatically and segmentally decreased gradually, for example, the frequency difference is decreased by 0.1 Hz each time.

Figure 4A:
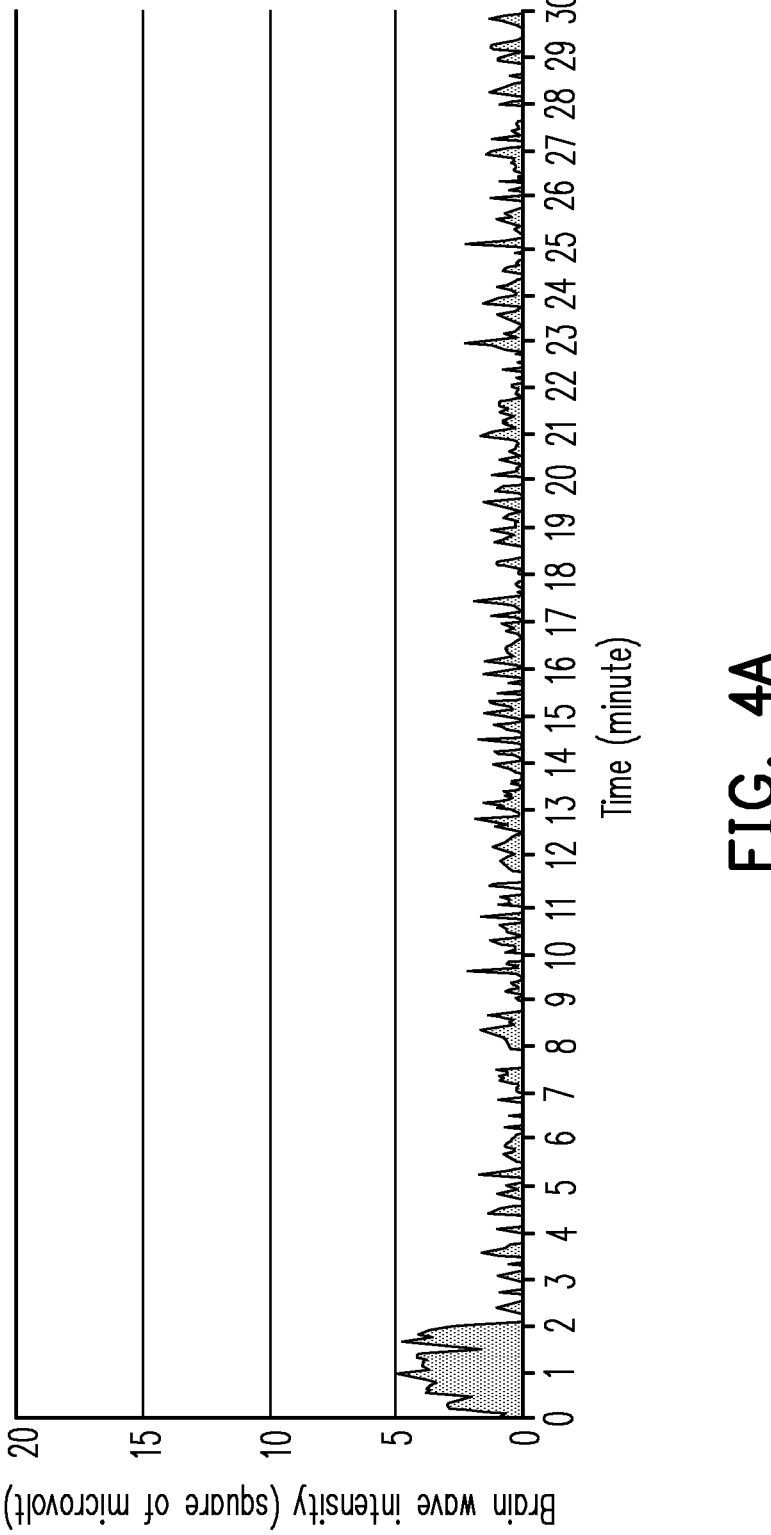
FIG. 4A is an experimental result of a comparative example 3 using the brain wave induction method of the prior art.

FIG. 4A is an experimental result of a comparative example 3 using the brain wave induction method of the prior art. In comparative example 3, the frequency difference is kept constant at 2 Hz. Referring to FIG. 4A, within 30 minutes of continuously inputting the frequency difference, δ waves are induced in the testee's brain only in the first 2 minutes. However, after 2 minutes of the experiment, it is almost impossible for the δ wave to be induced in the testee's brain.

Figure 4B:
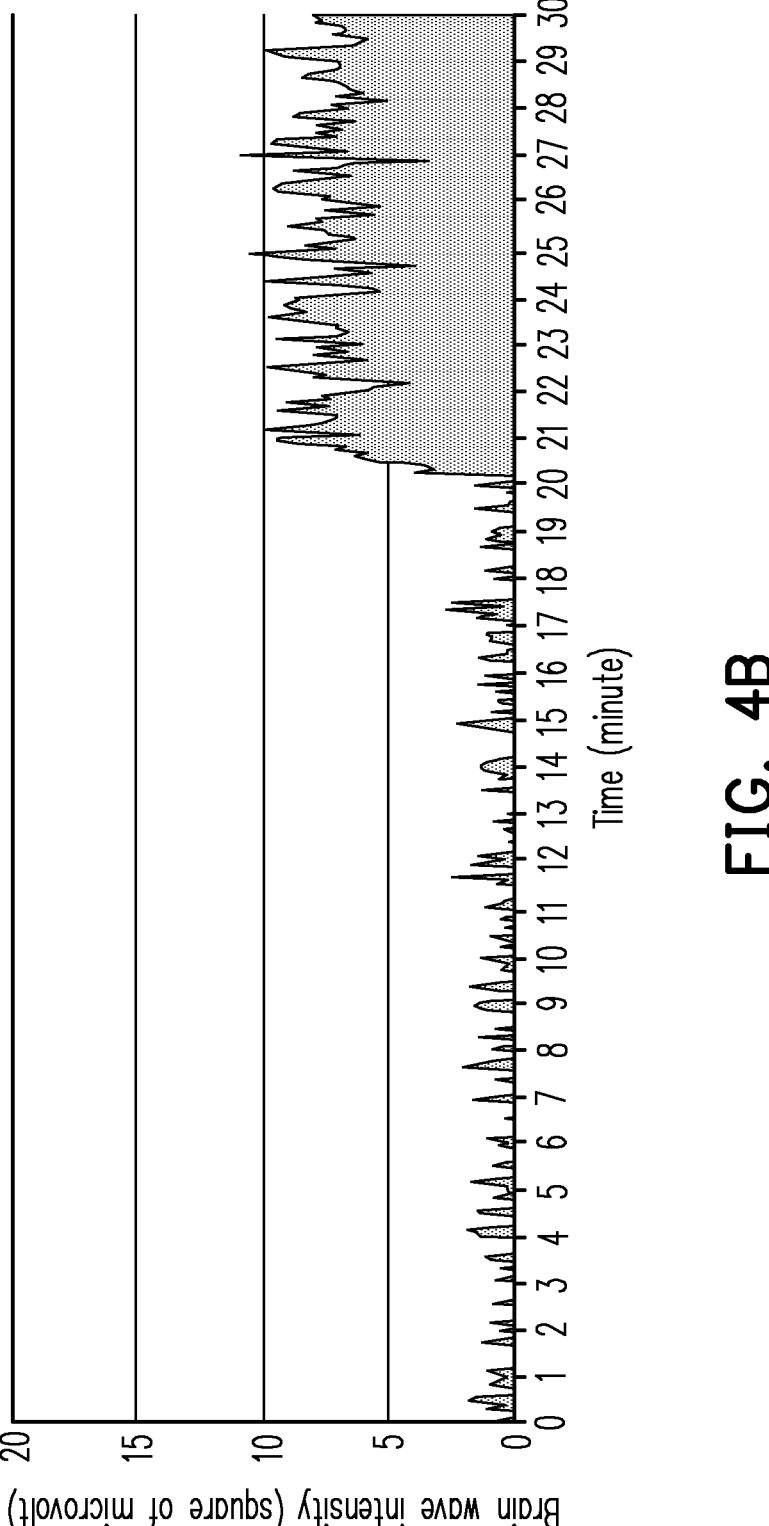
FIG. 4B is an experimental result of an experimental example 5 using the brain wave induction method of the embodiment.

Conversely, in the brain wave induction method of the embodiment, the frequency difference between the first frequency and the second frequency is automatically gradually decreased along with time. FIG. 4B is an experimental result of an experimental example 5 using the brain wave induction method of the embodiment. The testees in the comparative example 3 and the experimental example 5 are the same person. In the experimental example 5, the frequency difference is automatically and segmentally decreased from 12 Hz to 0.5 Hz gradually, a change amount of each change in the frequency difference is 0.1 Hz, and the same frequency difference is remained unchanged for 16 seconds after each change. Referring to FIG. 4B, during the first 20 minutes of continuously inputting the frequency difference in the manner of the experimental example 5, since the difference between the frequency difference and the δ wave is relatively large, it is almost impossible for the δ wave to be induced in the testee's brain. However, after 20 minutes of the experiment, δ waves could be detected in the testee's brains most of the time, and the energy of the detected induced δ waves is particularly high. This is because that the brain wave induction method of the embodiment induces the subjects with automatically gradually decreased frequency differences, so that better induction effects may be produced at multiple frequency differences, and good brain wave induction effects are produced in a longer period of time.

Comparing the experimental result of the comparative example 3 in FIG. 4A and the experimental result of the experimental example 5 in FIG. 4B, it may be clearly seen that the brain wave induction method of the embodiment is significantly more efficient in inducing brain waves than the prior art. Namely, in the brain wave induction method of the embodiment, the automatic gradual decrease of the frequency difference along with time may obviously and effectively induce brain waves.

Figure 5A:
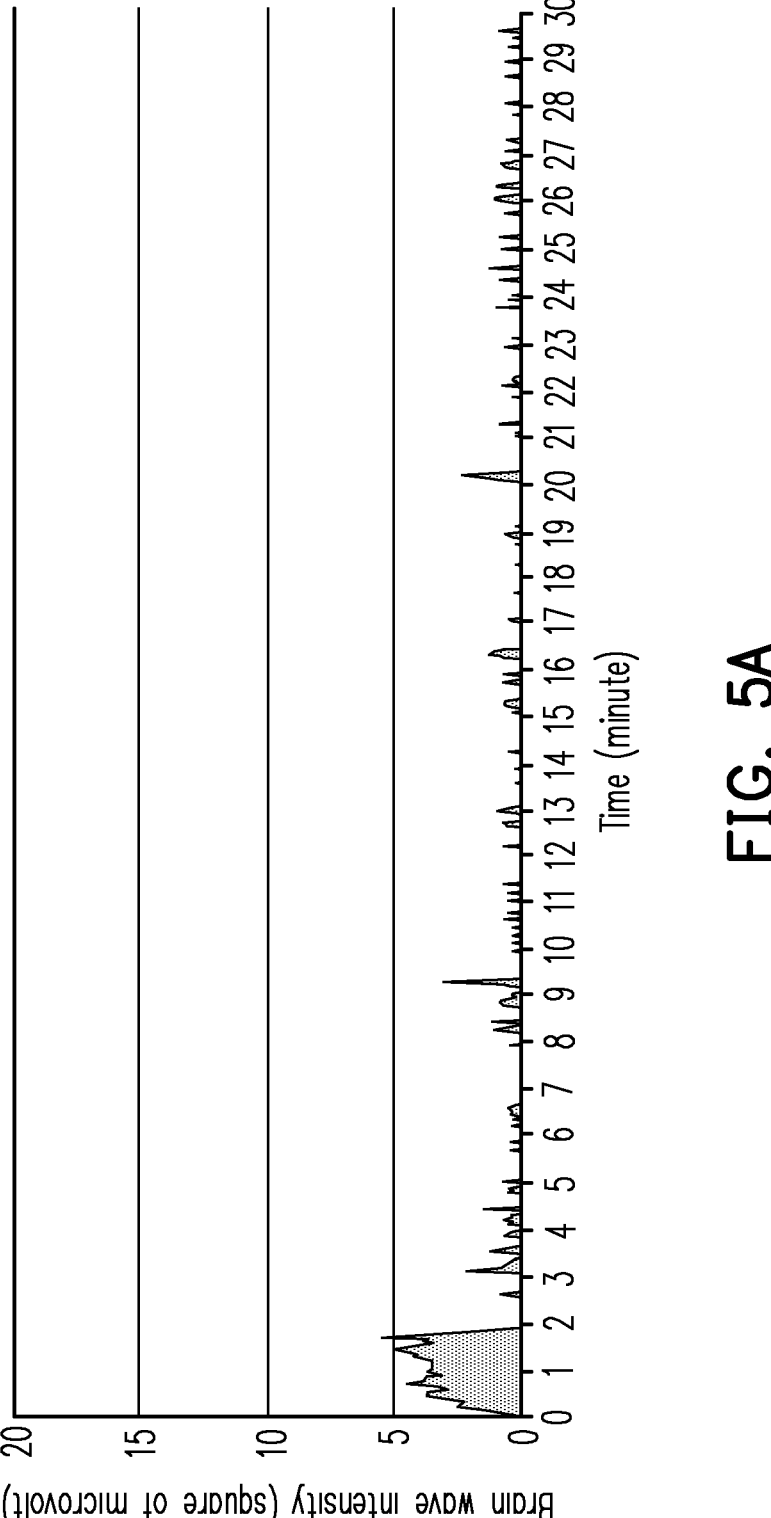
FIG. 5A is an experimental result of a comparative example 4 using the brain wave induction method of the prior art.

FIG. 5A is an experimental result of a comparative example 4 using the brain wave induction method of the prior art. In the comparative example 4, the frequency difference is kept constant at 2 Hz, but a testee is different from the testee of the comparative example 3. Referring to FIG. 5A, similar to the comparative example 3, within 30 minutes of continuously inputting such frequency difference, δ waves are induced in the brain of the testee only in the first 2 minutes. However, after 2 minutes of the experiment, it was almost impossible for the δ wave to be induced in the testee's brain.

Figure 5B:
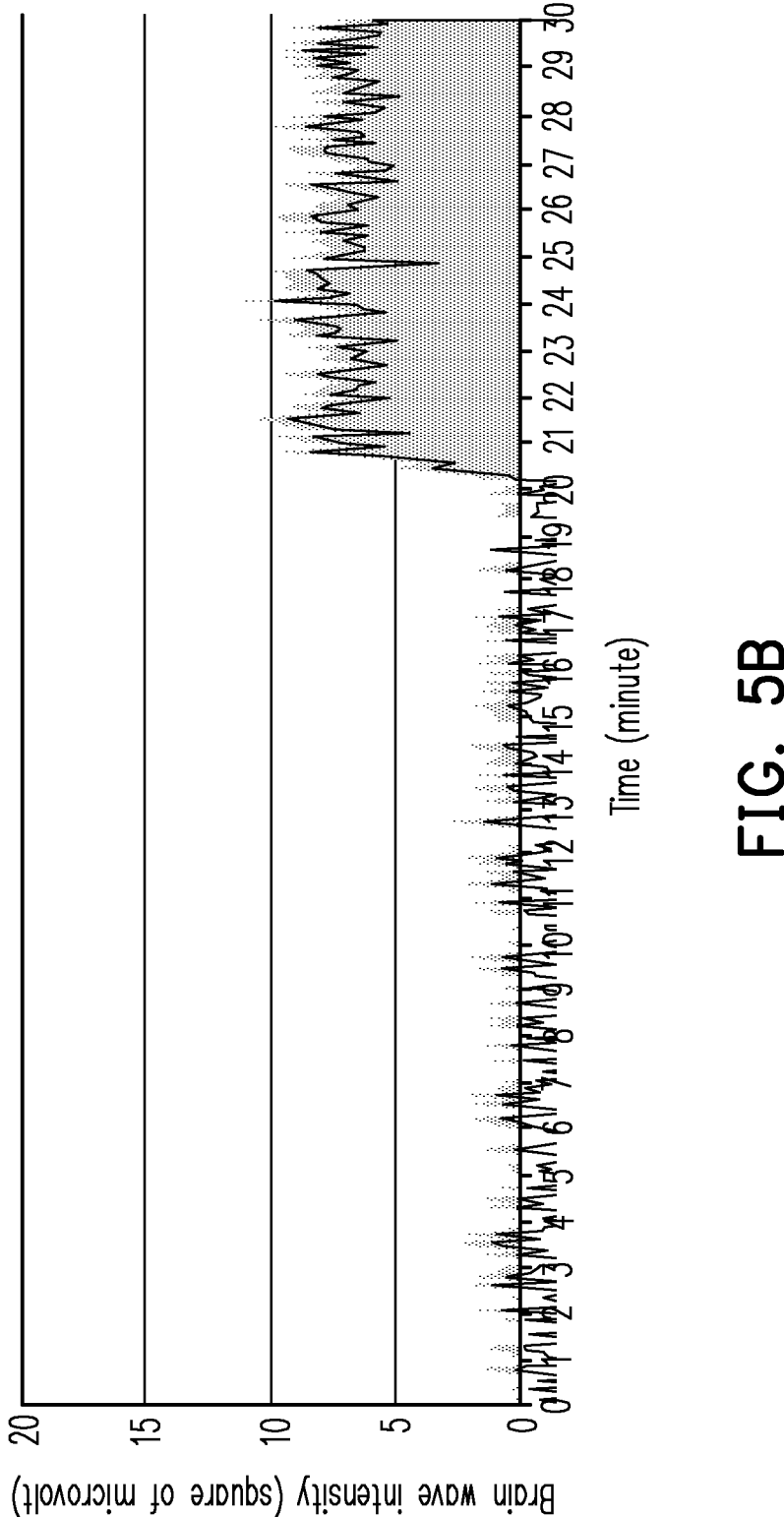
FIG. 5B is an experimental result of an experimental example 6 using the brain wave induction method of the embodiment.

FIG. 5B is an experimental result of an experimental example 6 using the brain wave induction method of the embodiment. The testees in the comparative example 4 and the experimental example 6 are the same person. In the experiment 6, the frequency difference is automatically and segmentally decreased from 12 Hz to 0.5 Hz gradually, a change amount of each change in the frequency difference is 0.1 Hz, and the same frequency difference is remained unchanged for 16 seconds after each change. Referring to FIG. 5B, similar to the experimental example 5, during the first 20 minutes of continuously inputting the frequency difference in the manner of the experimental example 6, since the difference between the frequency difference and the δ wave is relatively large, it is almost impossible for the δ wave to be induced in the testee's brain. However, after 20 minutes of the experiment, δ waves could be detected in the testee's brains most of the time, and the energy of the detected induced δ waves is particularly high.

Comparing the experimental result of the comparative example 4 in FIG. 5A and the experimental result of the experimental example 6 in FIG. 5B, it may be clearly seen that the brain wave induction method of the embodiment is more efficient in inducing brain waves than the prior art. Namely, in the brain wave induction method of the embodiment, the automatic gradual decrease of the frequency difference along with time may obviously and effectively induce brain waves.

In summary, in the brain wave induction method of the invention, since the frequency difference is changed automatically along with time, even if different users have different brain wave induction effects after receiving different frequency differences, most of them may be induced with target brain waves by their more sensitive frequency differences by changing the frequency difference. Moreover, the frequency difference that each user is more sensitive to may not be a single specific value but multiple specific values, and since the brain wave induction method of the invention uses the frequency difference that changes automatically along with time, it may correspond to the correct frequency difference one by one to induce the target brain wave, and increase the time for successful brain wave induction.

What is claimed is:

1. A brain wave induction method, comprising:

simultaneously providing a first sound wave to a left ear of a user and a second sound wave to a right ear of the user, wherein there is a frequency difference between a first frequency of the first sound wave and a second frequency of the second sound wave, and the frequency difference is automatically changed along with time, wherein the frequency difference is changed back and forth between 0.5 Hz and 4 Hz, between 4 Hz and 8 Hz, between 8 Hz and 12 Hz, or between 12 Hz and 20 Hz, wherein the first sound wave and the second sound wave are respectively provided to the left ear and the right ear of the user through an earphone.

2. The brain wave induction method according to claim 1, wherein the frequency difference is changed multi-segmentally along with time.

3. The brain wave induction method according to claim 1, wherein the frequency difference is remained unchanged for 5 seconds to 120 seconds after each change.

4. The brain wave induction method according to claim 1, wherein a change amount of each change in the frequency difference is 0.1 Hz, 0.2 Hz, 0.5 Hz, or 1 Hz.

5. The brain wave induction method according to claim 1, wherein a change amount of each change in the frequency difference is between 0.1 Hz and 1 Hz.

6. The brain wave induction method according to claim 1, wherein the frequency difference is reduced by 0.1 Hz each time.

7. The brain wave induction method according to claim 1, wherein the frequency difference is remained unchanged for 16 seconds after each change.

8. The brain wave induction method according to claim 1, wherein the earphone has an active noise cancellation function.

9. The brain wave induction method according to claim 1, wherein the earphone is a wireless earphone.

10. The brain wave induction method according to claim 1, wherein the earphone is a Bluetooth earphone.

11. The brain wave induction method according to claim 1, wherein after respectively providing the first sound wave and the second sound wave to the left ear and the right ear of the user for a predetermined time, provision of the first sound wave and the second sound wave is automatically stopped.

12. The brain wave induction method according to claim 1, wherein the first sound wave and the second sound wave are respectively generated after performing a frequency adjustment on a self-selected audio of the user.

13. The brain wave induction method according to claim 1, further comprising: providing a first background sound wave to the left ear of the user and a second background sound wave to the right ear of the user while providing the first sound wave and the second sound wave, wherein the frequency difference is provided between a third frequency of the first background sound wave and a fourth frequency of the second background sound wave.

* * * * *